United States Patent [19]
Ponsford et al.

[11] Patent Number: 6,031,142
[45] Date of Patent: Feb. 29, 2000

[54] ALTERNATIVE SOLVENTS FOR A METHOD OF RECLAIMING STYRENE AND OTHER PRODUCTS FROM POLYSTYRENE BASED MATERIALS

[76] Inventors: Thomas E. Ponsford; Henry T. Ponsford, both of 14112 Durhullen Dr., Poway, Calif. 92064

[21] Appl. No.: 09/150,604

[22] Filed: Sep. 10, 1998

Related U.S. Application Data

[60] Provisional application No. 60/058,502, Sep. 11, 1997.

[51] Int. Cl.[7] .................................................. C07C 1/00
[52] U.S. Cl. ............................................................. 585/241
[58] Field of Search ............................................. 585/241

[56] References Cited

U.S. PATENT DOCUMENTS

| | | | |
|---|---|---|---|
| 2,372,527 | 3/1945 | Soday | 260/669 |
| 2,372,528 | 3/1945 | Soday | 260/669 |
| 2,383,922 | 8/1945 | Soday | 260/669 |
| 3,692,858 | 9/1972 | Brewer et al. | |
| 3,985,820 | 10/1976 | Albright et al. | |
| 4,375,570 | 3/1983 | Yudovich | |
| 5,223,543 | 6/1993 | Iovino | 521/44.5 |
| 5,288,934 | 2/1994 | de Broqueville | 585/241 |
| 5,406,010 | 4/1995 | Ponsford et al. | 585/241 |
| 5,502,263 | 3/1996 | Ponsford et al. | |
| 5,672,794 | 9/1997 | Northemann | 585/241 |

*Primary Examiner*—Walter D. Griffin
*Assistant Examiner*—Thuan D. Dang
*Attorney, Agent, or Firm*—Foley & Lardner

[57] ABSTRACT

A method of pretreating polystyrene-containing materials to form a solution of polystyrene in a processing solvent from which the styrene in the polystyrene in the materials is reclaimed. The materials are mixed with an environmentally acceptable pretreating solvent having a lower boiling point than the processing solvent, typically at a location remote from the reclamation plant. The pretreating solvent is selected from the group consisting of d-limonene, l-limonene, dipentene, and blends thereof. Prior to actual processing to reclaim styrene, the pretreating solvent is substantially replaced with the processing solvent. The pretreating solvent may be recovered for reuse.

28 Claims, 1 Drawing Sheet

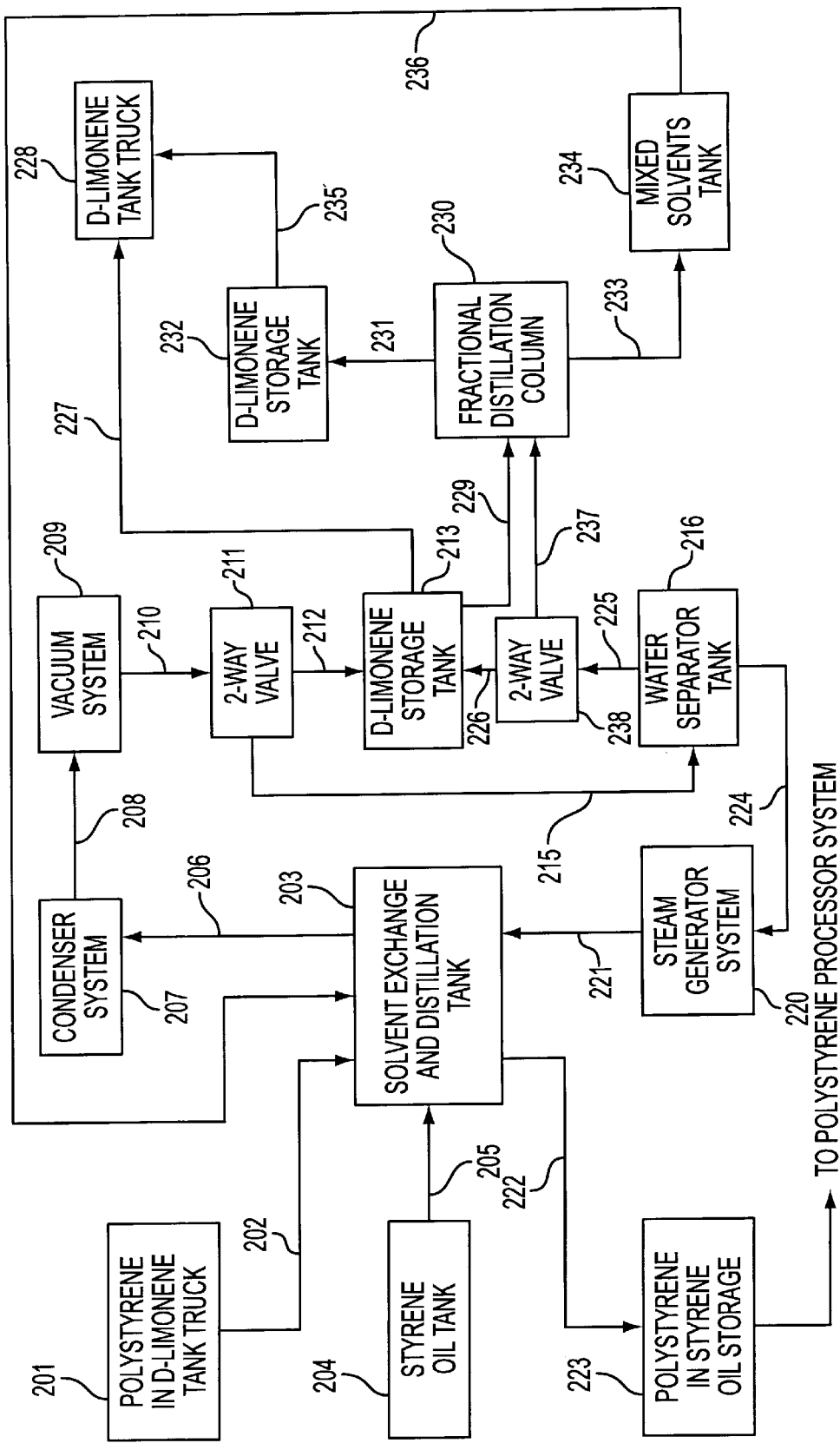
FIGURE

ALTERNATIVE SOLVENTS FOR A METHOD OF RECLAIMING STYRENE AND OTHER PRODUCTS FROM POLYSTYRENE BASED MATERIALS

This application is based on and claims the benefit of provisional application Ser. No. 60/058,502, filed Sep. 11, 1998.

BACKGROUND OF THE INVENTION

1. Field of the Invention

This invention relates to a method of reclaiming styrene and other products from polystyrene based materials. In particular, the invention relates to use of solvents approved by governmental agencies to be of low toxicity in a pre-treatment container used to receive the materials to be depolymerized.

2. Description of Related Art

U.S. Pat. No. 5,502,263 (the '263 patent) describes a process for recycling polystyrene trash using a manufactured liquid, "styrene oil" (defined in the '263 patent), as a solvent for the polystyrene during the processing. A preferred embodiment of that recycling process involves placing a dissolving tank, equipped with a removable lid and partially filled with styrene oil, in each industrial or commercial site which routinely discards polystyrene, especially foamed polystyrene. An employee of each site would place its discards into the local dissolving tank as they are discarded, thus eliminating the need for voluminous storage space for discards between trash collections, and also substantially reducing the cost of trash collection. Moreover, the use of styrene oil as an aid in collecting the discards is doubly useful, as it is not only a strong solvent for polystyrene, but also greatly assists in the later processing of the polystyrene into styrene monomer.

Although styrene oil is believed to have a very low toxicity, its toxicity has not yet been officially established by the Environmental Protection Agency or OSHA. Should a significant delay occur in obtaining approval for the use of styrene oil in dissolving tanks, which are frequently opened within occupied facilities, the use of this particularly efficient method of trash collection may be precluded for some time. Therefore, there exists a need for a pre-processing method using a solvent that already has been governmentally approved for use within occupied facilities.

SUMMARY OF THE INVENTION

The invention is a pre-processor subsystem, or collector system, which uses an alternate solvent, i.e., a solvent other than styrene oil, to dissolve polystyrene. The polystyrene then is transferred from the alternate solvent to the styrene oil for depolymerization.

The alternative solvent is used for the collection of polystyrene discards and trash at the collection sites. The resulting solution is collected, typically by tank trucks, all in accordance with the collection process described in the '263 patent. If desired, the pre-processor subsystem of the invention also can be co-located with the polystyrene processing plant described in the '263 patent.

An alternative solvent used to collect and transport dissolved polystyrene may not be suitable for use in place of or with styrene oil when polystyrene-containing solution is heated in the depolymerization step in the practice of the method of the '263 patent. The entirety of the '263 patent is incorporated by reference herein. Typically, such alternate solvents decompose or degrade at a temperature lower than the temperature at which the depolymerization step of the method of the '263 patent is carried out.

In accordance with the method of this invention, the polystyrene-containing alternate solvent is treated so as to transfer the dissolved polystyrene to styrene oil before depolymerization of the polystyrene. In particular, a suitable alternate solvent is compatible with that part of the polystyrene processing system described in the '263 patent before the depolymerization of the styrene and is amenable to treatment to cause significantly complete transfer of the dissolved polystyrene from the alternative solvent to styrene oil. Thus-transferred polystyrene then is depolymerized in accordance with the depolymerization portion of the method of the '263 patent. The invention also relates to the method of using the subsystem.

Because many alternative solvents are not suitable for the subsequent processing of polystyrene described in the '263 patent, a pre-processor subsystem must be used to transfer the dissolved polystyrene from solution in alternative solvent to solution in styrene oil, and to recover and purify the alternative solvent for continued use as a solvent. This subsystem must be contained so that styrene oil will not be released to the environment during the transfer operations.

The subsystem of the invention is designed in a modular fashion so that it can be configured as desired to remove styrene oil contaminant from the reclaimed alternative solvent to a required level of purity. This flexibility is useful, not only because a processor then can obtain a preferred desired purity, but also because a governmentally-mandated purity standard may be enacted, or an existing standard changed, at any time.

One aspect of the invention provides a method of pretreating polystyrene-containing materials to form a solution of polystyrene in a processing solvent from which the styrene in the polystyrene in the materials is reclaimed. The materials are mixed with a pretreating solvent selected from the group consisting of d-limonene, l-limonene, dipentene, and blends thereof, to dissolve the polystyrene and form a solution of polystyrene in pretreating solvent. The pretreating solvent is substantially replaced with the processing solvent to form the solution of polystyrene in processing solvent. The processing solvent has a higher boiling point than the pretreating solvent.

The processing solvent preferably is styrene oil, as defined in the '263 patent. The pretreating solvent may be recovered for reuse.

Another aspect of the invention provides the above-described pretreating method as part of an overall method of reclaiming styrene from polystyrene-containing materials.

A third aspect of the invention provides a method of pretreating polystyrene-containing materials prior to depolymerization to reclaim styrene from the polystyrene in the materials, wherein the materials are mixed with dipentene to dissolve the polystyrene and form a solution of polystyrene in dipentene.

BRIEF DESCRIPTION OF THE DRAWING

The single FIGURE is a schematic flow diagram of a preferred embodiment of the method of the invention, as applied to the transfer of polystyrene from a solution of polystyrene in d-limonene to a solution of polystyrene in styrene oil, with the d-limonene reclaimed and purified for future use.

DETAILED DESCRIPTION OF A PREFERRED EMBODIMENT

The inventors have discovered that d-limonene, or with llimonene, in its racemic form, dipentene, are especially suitable alternative solvents for use in the present invention. D-limonene, an oily solvent obtained by processing citrus peels, particularly orange peels, has a very low toxicity and has been used commercially for many years both as a solvent in various processes and as an orange flavoring agent in foods. D-limonene is relatively expensive and slightly less effective than styrene oil as a solvent for polystyrene, but it will serve as an alternate solvent to the styrene oil solvent, and it is now governmentally approved for use in an occupied facility.

To clarify the following description, a short discussion of selected alternate solvents is useful. D-limonene is a hydrocarbon compound in a class called monocyclic monoterpenes, which has unusual properties. All monoterpenes, which have the formula $C_{10}H_{16}$, are constructed of a "building block", $C_5H_8$, which is also the formula of an independent hydrocarbon compound, isoprene. Isoprene is widely used to make many petrochemical compounds, such as man-made "natural" rubber.

D-limonene is, in fact, a dimer of isoprene. D-limonene is one of a pair of "twin" compounds called enantiomers. Enantiomers are compounds having identical chemical formulas but chemical structures that are mirror images of each other. D-limonene is the dextrorotatory twin (rotates plane-polarized light to the right), and l-limonene is the levorotatory twin (rotates plane-polarized light to the left). Both of the limonenes occur in citrus peels, but d-limonene is much more prevalent. If d-limonene and l-limonene are present in equal parts, the mixture is said to be racemic. This racemic mixture is called dipentene.

D-limonene is prepared by crushing and then steam-distilling citrus peels. The resulting distillate is actually mostly d-limonene, but it also contains a minor percentage of l-limonene (which is inseparable from d-limonene for practical purposes), and a very small amount of other impurities. Governmental agencies have found this mixture to be essentially non-toxic, and its use as a food flavoring additive has been approved long ago. D-limonene is expensive, however, and is not extensively used as a commercial solvent.

Dipentene can be prepared by two different methods: by catalytically reacting turpentine at elevated temperature, or directly from isoprene. Dipentene made by either method is much less expensive than d-limonene. Since it has no desirable flavor, however, the principal use of dipentene is as a solvent in many processes; as such, it does not have to be highly refined. Historically, dipentene has been prepared from turpentine, and this "solvent grade" dipentene comprises about 95% dipentene and 5% mixed terpenes. The boiling points of these terpenes are very close to that of dipentene, and it is not worth the trouble of trying to remove them. Solvent grade dipentene has been characterized by the EPA as having moderately low toxicity, but not so low as pure dipentene; therefore, its early approval for use in the method of this invention is uncertain. The terpene impurities do not disqualify its use with the preferred embodiment of this invention, however.

Dipentene prepared from isoprene is very pure, and has been rated by governmental agencies as having a toxicity comparable to d-limonene. The isoprene process is more recent than that using turpentine, and a substantial manufacturing capability to perform the isoprene process has not been constructed to date. The process is not complex, however, and facilities could be readily constructed if a demand arose.

Although these two limonenes and dipentene can have differences in some properties, such as odor and flavor, they all exhibit very nearly the same basic physical and chemical properties, such as boiling points and behavior in solutions. For this reason, they are chemically interchangeable as solvents for use in the invention. The reasons for distinguishing between them are legal (governmentally approved low toxicity) and economic, and are significant.

This unusual situation makes the invention more flexible in use. The following table may assist the skilled practitioner to select the proper alternative solvent for collection of polystyrene:

| Alternate Solvent | Relative Cost | Toxicity | Availability |
| --- | --- | --- | --- |
| d-limonene | High | Acceptable | Now |
| Pure dipentene from isoprene | Low | Acceptable | Soon |
| Solvent grade dipentene | Low | Moderate | Now |

For convenience, the invention will be described as it relates to d-limonene. However, it should be understood that d-limonene represents any of the variants of the solvents d-limonene (with its impurities as approved for food use), l-limonene, mixtures at any ratio of the two limonenes, and dipentene (with its impurities as previously discussed). Also, in the following text, d-limonene can refer either to approved food-grade d-limonene as previously described, or to pure d-limonene, both of which will work well in the invention.

Because a governmentally allowed concentration of styrene oil contamination in recycled d-limonene has not been established, and may change from time to time in the future as more toxicity data becomes available, the preferred embodiment of a pre-processor subsystem of the invention described in detail herein is capable of producing recycled d-limonene over a wide range of purity, up to 99.9+% (less than 0.1% styrene oil). Clearly, other preferred embodiments can be designed for narrower ranges of purity if desired, with consequent simplification and reduced cost. This flexibility will be discussed in more detail after the preferred embodiment subsystem has been substantially described. With the guidance provided herein, skilled practitioners will be able to select an embodiment of the invention which will provide a desired degree of purity.

In accordance with the method of the invention, a solution of polystyrene in d-limonene is transferred from tank truck 201 through hose 202 to solvent exchange and distillation tank 203. Similarly, a supply of styrene oil is maintained in storage tank 204. Typically, this styrene oil was previously produced by the polystyrene process described in the '263 patent. An amount of styrene oil slightly less than the amount of d-limonene by weight is pumped from storage tank 204 into tank 203 through pipe 205. Tank 204 may be either an integral part of a polystyrene processing plant as described in the '263 patent or an integral part of the pre-processor subsystem of the invention. The absolute pressure in tank 203 then is reduced to approximately 1.5 psia through pipe 206, condenser system 207, and pipe 208 by vacuum system 209, which exhausts its flow through pipe 210, two-way valve 211, and pipe 212 to storage tank 213.

When the vacuum in solvent exchange tank 203 is established, the tank is purged with an inert gas to substantially purge oxygen therefrom, and then heated to approximately 100° C. by a heat transfer system 214 (not shown). The d-limonene in tank 203 begins to vaporize at the low pressure, and the vapor is drawn through pipe 206, condenser 207, and pipe 208 by vacuum system 209 in order to maintain the pressure in tank 203 at 1.5 psia.

The condensate in the vacuum system 209 is exhausted via pipe 210, two-way valve 211, and pipe 212 into storage tank 213. The styrene oil in tank 203 has a boiling point of approximately 215° C. at 1.5 psia, so only a small amount of styrene oil will vaporize during this distillation. As the ratio of d-limonene to styrene oil diminishes, the temperature of the liquid in tank 203 must be slowly increased in order to maintain an efficient rate of vaporization of d-limonene. The temperature is raised to approximately 125° C., when approximately 50% of the d-limonene has been vaporized. The purity of the initial d-limonene vapor is about 99.4% (0.6% styrene oil contaminant), and at this 50% point is about 98.8%, so the content of storage tank 213 is about 99.1% pure d-limonene. If 99.1% pure d-limonene is an acceptable degree of purity for use in industrial and commercial polystyrene dissolving tanks, or for any other use the operator contemplates, the 99.1% pure d-limonene in storage tank 213 is delivered through hose 227 to tank truck 228 or another satisfactory mode of transportation for delivery to the polystyrene collection sites, or for other use.

If the minimum acceptable degree of purity for use in dissolving tanks is higher than 99.1%, the d-limonene in storage tank 213 must be further purified. The content is pumped via pipe 229 to the center of a fractional distillation column 230. The fractional distillation column operates at a pressure of 1.5 psia, between temperatures of about 100° C. and 125° C. Approximately 99.99% pure d-limonene is drawn off the top of the column through pipe 231 to storage tank 232, and a small amount of a mixture of roughly 50% d-limonene and 50% styrene oil is drawn off the bottom of the column through pipe 233 to storage tank 234. Skilled practitioners are able to design and operate such a distillation column.

The 99.99% pure d-limonene in storage tank 232 is delivered periodically through hose 235 to tank truck 228 for delivery to the polystyrene collection sites or to other users. Clearly, the contents of storage tanks 213 and 232 can be blended to achieve intermediate standards of purity. The mixture of d-limonene and styrene oil in tank 234 is returned to solvent exchange tank 203 via pipe 236 for use in a later batch along with the charge of d-limonene/polystyrene solution from hose 202 and the styrene oil from pipe 205.

D-limonene is not very stable at elevated temperatures, and it is not desirable to raise its temperature above about 125° C. if it is to be repeatedly vaporized and reused. Accordingly, vaporization beyond this point is accomplished by steam distillation, using superheated steam generated in steam generator system 220, which receives its energy from heat transfer system 214 (not shown). After two-way valve 211 is switched to pipe 215, steam is introduced at approximately 125° C. and 1.5 psia into the bottom of tank 203 through pipe 221, where it bubbles up through the liquid and captures some d-limonene and a small amount of styrene oil, both as vapor. The mixed vapors are drawn into pipe 206 as before, condensed, and sent through two-way valve 211 and pipe 215 into water-separator tank 216. Steam distillation is continued at 125° C. until 99.99% of the d-limonene is removed from tank 203, and the polystyrene now is effectively dissolved in styrene oil. The vacuum system 209 and steam system 220 are turned off, and tank 203 is emptied through pipe 222 into styrene oil solution storage tank 223. Tank 223 can be an integral part of the polystyrene processor of the '263 patent, or an integral part of the pre-processor subsystem of this invention. The solution in styrene oil is removed as required from tank 223 to be sent to the polystyrene processor of the '263 patent.

The selections of 1.5 psia and 125° C. for the distillation of d-limonene used in the preceding description are preferred, as these conditions achieve an economical balance of several important parameters. In general, a steam distillation system becomes more efficient in usage of steam (lbs of steam required per lb of d-limonene distilled) as the temperature rises. An upper limit on the increase in temperature is imposed, however, by the rapidly increasing chemical instability of d-limonene above about 125° C., so 125° C. is the best temperature to use. Lower temperatures would result in a slower, less efficient process.

With regard to absolute pressure in the still, the amount of steam required to distill a pound of d-limonene decreases with decreasing still pressure (stronger vacuum), but a potential countering effect is the decrease in the condenser temperature required to maintain the desired vacuum. This desirable reduction in steam usage ratio is rapid down to about 1.5 psia, but levels out rather quickly below that absolute pressure. By coincidence, the steam condenser temperature required to maintain 1.5 psia in the still is about 46° C. (115° F.). This temperature is sufficiently above ambient temperature so that condensation can be achieved with an ambient temperature heat sink, either air or water. Operation at a lower temperature would require a refrigerated heat sink, resulting in significantly higher cost. In summary, 1.5 psia and 125° C. appear to be practical choices.

Returning to water separator tank 216, the liquid mixture of d-limonene, water, and a slight amount of styrene oil will separate at rest naturally into a lower layer of water and an upper layer of d-limonene/styrene oil mixture. At suitable intervals, water is drawn off the bottom of tank 216 and returned to the steam generator system 220 through pipe 224. The purity of d-limonene in the first steam distillate (after removal of water) is about 98.8%. The purity thereafter declines significantly as the d-limonene in tank 203 is exhausted, although the amount of styrene oil in the distillate is still small because the total hydrocarbon content of the vapor is also small.

If the governmentally approved purity of d-limonene to be used in polystyrene collection tanks is sufficiently low, there is opportunity for blending a very high purity stream and a lower purity stream in proportions sufficient to obtain or slightly exceed the desired value. In accordance with the method of the invention, d-limonene from tank 216 is pumped into tank 213 via pipe 225, valve 238 and pipe 226. The blended mixture would then be delivered in the usual way.

If the purity of d-limonene in tank 216 is too low to permit blending, the d-limonene in tank 216 must be further purified. The d-limonene in tank 216 is pumped into the fractional distillation column 230 via pipe 225, valve 238 and pipe 237, where it is purified and delivered via pipe 231, storage tank 232, and hose 235 to tank truck 228.

Other preferred embodiments are possible to meet other purity requirements. For example, if the required purity is expected to always exceed 99.1%, valve 211, pipe 212, storage tank 213, pipes 226 and 229, valve 238 and hose 227 can be eliminated, and all of the d-limonene produced can be sent to the fractional distillation column 230 for purification. Similarly, if the required purity is sufficiently low (about 95%) all of the previous eliminations, together with the fractional distillation column 230, storage tanks 232 and 234, pipes 225, 231, 233, 236 and 237, and hose 235, can be eliminated, and the upper part of water separator tank 216 can be directly connected with tank 228 by a new hose (not shown).

It will be apparent to those skilled in the art that various modifications to the above-described preferred embodiment may be made without departing from the true spirit and scope of the invention, which is to be limited only by the appended claims.

We claim:

1. A method of pretreating polystyrene-containing materials to form a solution of polystyrene in a processing solvent from which the styrene in the polystyrene in said materials is reclaimed, the method comprising the steps of:

mixing said materials with a pretreating solvent selected from the group consisting of d-limonene, l-limonene, dipentene, and blends thereof, to dissolve the polystyrene and form a solution of polystyrene in said pretreating solvent; and substantially replacing said pretreating solvent with said processing solvent to form said solution of polystyrene in said processing solvent, said processing solvent having a higher boiling point than said pretreating solvent.

2. The method of claim 1, wherein the step of substantially replacing said pretreating solvent with said processing solvent comprises the steps of:

adding a quantity of said processing solvent to said solution of polystyrene in pretreating solvent to form a dual-solvent polystyrene solution; and distilling said pretreating solvent from said dual-solvent polystyrene solution to form said solution of polystyrene in said processing solvent.

3. The method of claim 2, further comprising separately recovering said pretreating solvent.

4. The method of claim 2, wherein the quantity of said processing solvent added to said solution of polystyrene in pretreating solvent is approximately equal to the quantity of pretreating solvent by weight in said solution.

5. The method of claim 4, wherein said distillation step comprises the steps of:

reducing the pressure in a single-stage distillation tank containing said dual-solvent polystyrene solution to approximately 1.5 psia;

purging said tank with an inert gas to substantially remove oxygen therefrom;

heating said dual-solvent polystyrene solution to approximately 100° C. until about 50% of said pretreating solvent has been vaporized;

raising the temperature of said dual-solvent polystyrene solution to approximately 125° C. and simultaneously injecting superheated steam therethrough to extract an additional quantity of said pretreating solvent therefrom; and holding the temperature of said dual-solvent polystyrene solution at approximately 125° C. and continuing to inject superheated steam therethrough to extract substantially the remainder of said pretreating solvent therefrom.

6. The method of claim 2 wherein said distillation step comprises the steps of:

reducing the pressure in a single-stage-distillation tank containing said dual-solvent polystyrene solution to approximately 1.5 psia;

purging said tank with an inert gas to substantially remove oxygen therefrom;

heating said dual-solvent polystyrene solution to approximately 100° C. until about 50% of said pretreating solvent has been vaporized;

raising the temperature of said dual-solvent polystyrene solution to approximately 125° C. and simultaneously injecting superheated steam therethrough to extract an additional quantity of said pretreating solvent therefrom; and holding the temperature of said dual-solvent polystyrene solution at approximately 125° C. and continuing to inject superheated steam therethrough to extract substantially the remainder of said pretreating solvent therefrom.

7. The method of claim 6, further comprising separately recovering said pretreating solvent.

8. A method of pretreating polystyrene-containing materials to form a solution of polystyrene in styrene oil from which the styrene in the polystyrene in said materials is reclaimed, the method comprising the steps of:

mixing said materials with a pretreating solvent selected from the group consisting of d-limonene, l-limonene, dipentene, and blends thereof, to dissolve the polystyrene and form a solution of polystyrene in said pretreating solvent; and substantially replacing said pretreating solvent with styrene oil to form said solution of polystyrene in styrene oil.

9. The method of claim 8, wherein the step of substantially replacing said pretreating solvent with styrene oil comprises the steps of:

adding a quantity of styrene oil to said solution of polystyrene in pretreating solvent to form a dual-solvent polystyrene solution; and distilling said pretreating solvent from said dual-solvent polystyrene solution to form said solution of polystyrene in styrene oil.

10. The method of claim 9, further comprising separately recovering said pretreating solvent.

11. The method of claim 9, wherein the quantity of styrene oil added to said solution of polystyrene in pretreating solvent is approximately equal to the quantity of pretreating solvent by weight in said solution.

12. The method of claim 11, wherein said distillation step comprises the steps of:

reducing the pressure in a single-stage distillation tank containing said dual-solvent polystyrene solution to approximately 1.5 psia;

purging said tank with an inert gas to substantially remove oxygen therefrom;

heating said dual-solvent polystyrene solution to approximately 100° C. until about 50% of said pretreating solvent has been vaporized;

raising the temperature of said dual-solvent polystyrene solution to approximately 125° C. and simultaneously injecting superheated steam therethrough to extract an additional quantity of said pretreating solvent therefrom; and holding the temperature of said dual-solvent polystyrene solution at approximately 125° C. and continuing to inject superheated steam therethrough to extract substantially the remainder of said pretreating solvent therefrom.

13. The method of claim 9, wherein said distillation step comprises the steps of:

reducing the pressure in a single-stage distillation tank containing said dual-solvent polystyrene solution to approximately 1.5 psia;

purging said tank with an inert gas to substantially remove oxygen therefrom;

heating said dual-solvent polystyrene solution to approximately 100° C. until about 50% of said pretreating solvent has been vaporized;

raising the temperature of said dual-solvent polystyrene solution to approximately 125° C. and simultaneously injecting superheated steam therethrough to extract an additional quantity of said pretreating solvent therefrom; and holding the temperature of said dual-solvent polystyrene solution at approximately 125° C. and continuing to inject superheated steam therethrough to extract substantially the remainder of said pretreating solvent therefrom.

14. The method of claim 13, further comprising separately recovering said pretreating solvent.

15. In a method of reclaiming styrene from polystyrene-containing materials by heating under controlled conditions a solution of polystyrene from said materials in styrene oil to depolymerize the polystyrene, and separating the styrene therefrom, the improvement comprising the steps of:

pretreating the polystyrene-containing materials by mixing said materials with a pretreating solvent selected from the group consisting of d-limonene, l-limonene, dipentene, and blends thereof, to dissolve the polystyrene and form a solution of polystyrene in said pretreating solvent; and substantially replacing said pretreating solvent with styrene oil to form said solution of polystyrene in styrene oil.

16. The method of claim 15, wherein the step of substantially replacing said pretreating solvent with styrene oil comprises the steps of:

adding a quantity of styrene oil to said solution of polystyrene in pretreating solvent to form a dual-solvent polystyrene solution; and distilling said pretreating solvent from said dual-solvent polystyrene solution to form said solution of polystyrene in styrene oil.

17. The method of claim 16, further comprising separately recovering said pretreating solvent.

18. The method of claim 16, wherein the quantity of styrene oil added to said solution of polystyrene in pretreating solvent is approximately equal to the quantity of pretreating solvent by weight in said solution of polystyrene in pretreating solvent.

19. The method of claim 18, wherein said distillation step comprises the steps of:

reducing the pressure in a single-stage distillation tank containing said dual-solvent polystyrene solution to approximately 1.5 psia;

purging said tank with an inert gas to substantially remove oxygen therefrom;

heating said dual-solvent polystyrene solution to approximately 100° C. until about 50% of said pretreating solvent has been vaporized;

raising the temperature of said dual-solvent polystyrene solution to approximately 125° C. and simultaneously injecting superheated steam therethrough to extract an additional quantity of said pretreating solvent therefrom; and holding the temperature of said dual-solvent polystyrene solution at approximately 125° C. and continuing to inject superheated steam therethrough to extract substantially the remainder of said pretreating solvent therefrom.

20. The method of claim 16, wherein said distillation step comprises the steps of:

reducing the pressure in a single-stage distillation tank containing said dual-solvent polystyrene solution to approximately 1.5 psia;

purging said tank with an inert gas to substantially remove oxygen therefrom;

heating said dual-solvent polystyrene solution to approximately 100° C. until about 50% of said pretreating solvent has been vaporized;

raising the temperature of said dual-solvent polystyrene solution to approximately 125° C. and simultaneously injecting superheated steam therethrough to extract an additional quantity of said pretreating solvent therefrom; and holding the temperature of said dual-solvent polystyrene solution at approximately 125° C. and continuing to inject superheated steam therethrough to extract substantially the remainder of said pretreating solvent therefrom.

21. The method of claim 20, further comprising separately recovering said pretreating solvent.

22. In a method of reclaiming styrene from polystyrene-containing materials by heating under controlled conditions a solution of polystyrene from said materials in a processing solvent to depolymerize the polystyrene, and separating the styrene therefrom, the improvement comprising the steps of:

pretreating the polystyrene-containing materials by mixing said materials with a pretreating solvent selected from the group consisting of d-limonene, l-limonene, dipentene, and blends thereof, to dissolve the polystyrene and form a solution of polystyrene in said pretreating solvent; and substantially replacing said pretreating solvent with said processing solvent to form said solution of polystyrene in said processing solvent.

23. The method of claim 22, wherein the step of substantially replacing said pretreating solvent with said processing solvent comprises the steps of:

adding a quantity of said processing solvent to said solution of polystyrene in pretreating solvent to form a dual-solvent polystyrene solution; and distilling said pretreating solvent from said dual-solvent polystyrene solution to form said solution of polystyrene in said processing solvent.

24. The method of claim 23, further comprising separately recovering said pretreating solvent.

25. The method of claim 23, wherein the quantity of said processing solvent added to said solution of polystyrene in pretreating solvent is approximately equal to the quantity of pretreating solvent by weight in said solution of polystyrene in pretreating solvent.

26. The method of claim 25, wherein said distillation step comprises the steps of:

reducing the pressure in a single-stage distillation tank containing said dual-solvent polystyrene solution to approximately 1.5 psia;

purging said tank with an inert gas to substantially remove oxygen therefrom;

heating said dual-solvent polystyrene solution to approximately 100° C. until about 50% of said pretreating solvent has been vaporized;

raising the temperature of said dual-solvent polystyrene solution to approximately 125° C. and simultaneously injecting superheated steam therethrough to extract an additional quantity of said pretreating solvent therefrom; and holding the temperature of said dual-solvent polystyrene solution at approximately 125° C. and continuing to inject superheated steam therethrough to extract substantially the remainder of said pretreating solvent therefrom.

27. The method of claim 23, wherein said distillation step comprises the steps of:

reducing the pressure in a single-stage distillation tank containing said dual-solvent polystyrene solution to approximately 1.5 psia;

purging said tank with an inert gas to substantially remove oxygen therefrom;

heating said dual-solvent polystyrene solution to approximately 100° C. until about 50% of said pretreating solvent has been vaporized;

raising the temperature of said dual-solvent polystyrene solution to approximately 125° C. and simultaneously injecting superheated steam therethrough to extract an additional quantity of said pretreating solvent therefrom; and holding the temperature of said dual-solvent polystyrene solution at approximately 125° C. and continuing to inject superheated steam therethrough to extract substantially the remainder of said pretreating solvent therefrom.

28. The method of claim 27, further comprising separately recovering said pretreating solvent.

* * * * *